United States Patent [19]

Uemura

[11] Patent Number: 5,766,010

[45] Date of Patent: Jun. 16, 1998

[54] ARTIFICIAL TOOTH ROOT AND METHOD OF MANUFACTURING SAME

[75] Inventor: Yuji Uemura, Gunma, Japan

[73] Assignee: Daiichi Forging Co., Ltd., Japan

[21] Appl. No.: 832,498

[22] Filed: Apr. 3, 1997

[30] Foreign Application Priority Data

May 27, 1996 [JP] Japan .................. 8-132114

[51] Int. Cl.$^6$ .................................. A61C 8/00
[52] U.S. Cl. ........................... 433/175; 433/173
[58] Field of Search .................. 433/172, 173, 433/175, 201.1

[56] References Cited

U.S. PATENT DOCUMENTS

| | | | |
|---|---|---|---|
| 3,628,248 | 12/1971 | Kroder | 433/175 |
| 4,178,686 | 12/1979 | Riess et al. | 433/173 X |
| 4,195,409 | 4/1980 | Child | 433/175 |
| 4,199,864 | 4/1980 | Ashman | 433/175 |
| 4,613,308 | 9/1986 | Ehrl | 433/173 |
| 5,094,618 | 3/1992 | Sullivan | 433/173 |
| 5,639,237 | 6/1997 | Fontenot | 433/173 |

FOREIGN PATENT DOCUMENTS

| | | |
|---|---|---|
| 4-49958 | 2/1992 | Japan . |
| 6-154246 | 6/1994 | Japan . |
| 7-36827 | 4/1995 | Japan . |

*Primary Examiner*—Nicholas D. Lucchesi
*Attorney, Agent, or Firm*—Haynes and Boone, L.L.P.

[57] ABSTRACT

An artificial tooth root comprises a substantially cylindrical root part to be imbedded in a jaw bone, and a substantially cylindrical crown part to be projected out of a jaw bone and to be provided with a dental prosthesis. The root part is constituted by a base member provided with a multiplicity of convexities or concavities having a substantially identical configuration and being arranged with even intervals on the same axes apart from the central axis of the root part and with even intervals on the same circumferences. The convexities or concavities on a circumference and the ones on the neighboring circumference are alternately arranged, and the boundaries between the convexities or concavities and the base member are formed by smoothly curved surfaces.

12 Claims, 7 Drawing Sheets

ARTIFICIAL TOOTH ROOT AND METHOD OF MANUFACTURING SAME

BACKGROUND OF THE INVENTION

The present invention relates to a rod-like artificial tooth root and a method of manufacturing such an artificial tooth root which is so designed as to be easily treated when imbedded.

Among conventional artificial tooth roots are ones such as described for example, in Japanese Patent Publication No.7-36827 and Japanese Patent Laid-Open Publication No.6-154246. The artificial tooth root described in Japanese Patent Publication No.7-36827 includes a cylindrical implant body which is provided with a spiral projecting portion or annular projecting portions which increase the force of connection with the hard periodontium of an organism so that the implant body can be fixed to it in position securely. On the other hand, the artificial tooth root described in Japanese Patent Laid-Open Publication No.6-154246 includes a cylindrical implant body in which protrusions and recesses are alternately formed along the central axis in order to make it possible to generate such a tissue as a periodontal ligament between the implant body and a bone after the artificial tooth root has been implanted and to permit to keep the bone generation as well as the bone reconstruction stable for a long time.

The implant body disclosed in Japanese Patent Publication No.7-36827 has such a problem that stress is concentrated at corners of the implant body by the fixation to the hard periodontium of an organism, thus there is a tendency that the implant body itself is likely to be broken or parts of bone are likely to be damaged.

The implant body disclosed in Japanese Patent Laid-Open Publication No.6-154246 has such a problem that the cylindrical implant body is permitted the movement to some degree in order to generate a periodontium, thus the implant body cannot sufficiently be stabilized after the artificial tooth root has been implanted because of no force for restraining the rotation around the central axis.

SUMMARY OF THE INVENTION

Accordingly, it is a first object of the present invention to provide an artificial tooth root and a method of manufacturing same which can solve the above problem of the conventional art by facilitating to stabilize the implant body when imbedded and by promoting adhesion of a bone to the implant body as time elapses.

It is a second object of the present invention to provide an artificial tooth root which can effectively grow a compact superficial bone along the surface, can prevent from giving rise to a stress concentration on the bone around the imbedded part and causing the local destruction by an alternate arrangement of a plenty of convexities or concavities which are smoothly formed.

It is a third object of the present invention to provide an artificial tooth root which can give suitable stimulation to the surrounding bone around the imbedded part, can promote metabolism, can keep the surrounding superficial bone around the imbedded part healthy, can restrain a vertical motion along the central axis and a rotational motion around the central axis surely, can facilitate the fixation when imbedded, and can quicken the adhesion to a bone with time, by alternate arrangement of a plenty of convexities or concavities which are formed by smoothly curved surface.

It is a fourth object of the present invention to provide an artificial tooth root that can effectively and uniformly distribute the load, can prevent from loading overweight locationally, can distribute a force for fixing, can prevent from located destruction, and can facilitate growing of surrounding bone and holding the artificial tooth root, by regular arrangement of convexities or concavities on the root part.

It is a fifth object of the present invention to provide an artificial tooth root which can reduce the labor of implanting, by making no use of a tap whose size is equal to that of the screw of the implant.

It is a sixth object of the present invention to provide an artificial tooth root which can reduce the labor of implanting and can give the force for fixing which is same degree as the conventional implant body of screw and securer than the conventional cylindrical implant body when imbedded, by driving of a hammer without room of a prepared hole for reduction of the resistance on the occasion of insertion with touching only each point end of convexities with the prepared hole.

It is a seventh object of the present invention to provide an artificial tooth root which can uniformly distribute a load around the imbedded part, can hold the root of tooth along the central axis and around the central axis, and can easily take out a green part from a mold.

It is an eighth object of the present invention to provide an artificial tooth root which can improve the mass productivity, and can reduce a cost.

It is a ninth object of the present invention to provide an artificial tooth root which can facilitate to form a complicated shape, to remove a mold, and to combine with various artificial teeth, and can make the medical treatment easier and simpler.

It is a tenth object of the present invention to provide an artificial tooth root which can reduce the labor of processing on the occasion of covering a dental prosthesis.

It is an eleventh object of the present invention to provide an artificial tooth root which can simplify the form of mold and can make mold inexpensively and easily.

It is a twelfth object of the present invention to provide an artificial tooth root which makes it possible to distribute a load of the artificial tooth root finely and more uniformly, to transmit the load to a jaw bone, to distribute more uniformly, and to grow the superficial bone smoothly by increasing the number of convexities or concavities and by reducing the size of convexities or concavities.

It is a thirteenth object of the present invention to provide an artificial tooth root which makes it possible to remove the parts of extremely small radius of curvature and the square parts, to distribute the load of the artificial tooth root properly and uniformly, to transmit the distributed load to a jaw bone, to grow such a tissue as a periodontal ligament around the root part more effectively after having been implanted, and to obtain a connective tissue suitable for chewing, by joining the convexities or concavities to the base member with the smoothly curved surface having substantially even radius of curvature one another.

It is a fourteenth object of the present invention to provide an artificial tooth root which makes it possible to facilitate the forming of the artificial tooth root by removing the undercut in case of injection molding.

It is a fifteenth object of the present invention to provide an artificial tooth root which makes it possible not to be damaged easily, and not to affect to an organism badly by using firm and bio-compatible materials.

It is a sixteenth object of the present invention to provide a manufacturing method of an artificial tooth root which makes to it possible to form the products with a complicated shape difficult to process easily, and to improve the mass productivity, and to reduce a cost.

It is a seventeenth object of the present invention to provide a manufacturing method of an artificial tooth root which makes it possible to produce a mold for the artificial tooth root with complicated shape easily, to be taken out from a mold easily, to enhance the productivity, and to reduce a cost.

According to a first aspect of the invention, the above-mentioned first to six objects are achieved by providing an artificial tooth root comprising substantially cylindrical root part to be imbedded in a jaw bone, and a substantially cylindrical crown part to be projected out of the jaw bone and to be provided with a dental prosthesis, wherein said root part is constituted by a base member provided with a multiplicity of convexities or concavities having substantially identical configuration and being disposed with even intervals on the same axes apart from the central axis of the root part and with even intervals on the same circumferences, the convexities or concavities on a circumference and the ones on the neighboring circumference are alternately arranged, and the boundaries between the convexities or concavities and the base member are formed by smoothly curved surface.

According to a second aspect of the invention, the above-mentioned seventh object is achieved by providing the artificial tooth root wherein the number of the convexities or concavities having substantially identical configuration is multiple of three.

According to a third aspect of the invention, the above-mentioned eighth object, by providing the artificial tooth root wherein said root part and said crown part are defined as a unitary body.

According to a fourth aspect of the invention, the above-mentioned ninth object is achieved by providing the artificial tooth root wherein the root part and the crown part are defined as separate bodies and are free to be connected with each other and separated from each other.

According to a fifth aspect of the invention, the above-mentioned tenth object is achieved by providing the artificial tooth root wherein said crown part has a cylindrical portion and a truncated-conical portion.

According to a sixth aspect of the invention, the above-mentioned eleventh object is achieved by providing the artificial tooth root wherein the number of the convexities or concavities which are disposed on the same circumference with even intervals is three, the convexities or concavities have substantially identical configuration, the convexities or concavities to be disposed on the other axes which are placed at angle of 60 degrees from said axis with the central axis of cylindrical part, are disposed on the circumference which is located in the intermediate position between two neighboring convexities or concavities on the same axis, and the convexities or concavities on a circumference and the ones on the neighboring circumference are alternately arranged and are shifted through angle of 60 degrees with the central axis.

According to a seventh aspect of the invention, the above-mentioned twelfth object is achieved by providing the artificial tooth root wherein the number of the convexities or concavities which are disposed on the same circumference with even intervals is six, the convexities or concavities have substantially identical configuration, the convexities or concavities to be disposed on the other axes which are placed at angle of 30 degrees from said axis with the central axis of cylindrical part, are disposed on the circumference which is located in the intermediate position of two neighboring convexities or concavities on the same axis, and the convexities or concavities on the circumference and the ones on the neighboring circumference are alternately arranged and shifted through angle of 30 degrees with the central axis.

According to an eighth aspect of the invention, the above-mentioned thirteenth and fourteenth objects are achieved by providing the artificial tooth root wherein convexities or concavities and the base member can be smoothly joined with uniform radius of curvature.

According to a ninth aspect of the invention, the above-mentioned fifteenth object is achieved by providing the artificial tooth root wherein the root part is made of such farm and bio-compatible materials as titanium, titanium oxide, or aluminium oxide.

According to a tenth aspect of the invention, the above-mentioned sixteenth object is achieved by providing a method of manufacturing an artificial tooth root comprising mixing a powdered material with a binder which is mainly made of resin, and molding the mixture by injection molding.

According to an eleventh aspect of the invention, the above-mentioned seventeenth object is achieved by providing the method of manufacturing artificial tooth root wherein said root part is molded by using the injection molding of the powdered materials, by means of a split mold whose number of segments is selected to be an aliquot with respect to the number of convexities or concavities on a circumference.

DETAILED DESCRIPTION OF THE PREFERRED EMBODIMENT

The invention will be explained with respect to embodiments in which each includes a cylindrical implant body having outside diameter 4 mm. However, it is to be understood that the present invention is by no means limited thereto.

Figure 1:
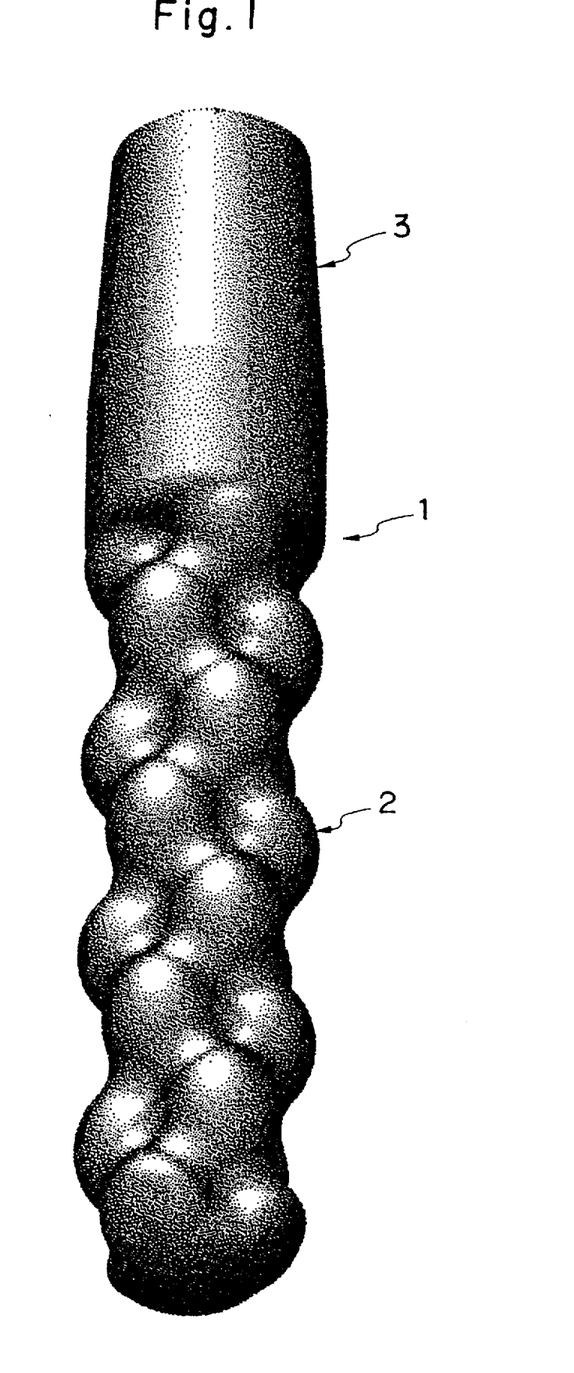
FIG. 1 is a perspective view of the artificial tooth root according to a first embodiment of the present invention.
Figure 2:
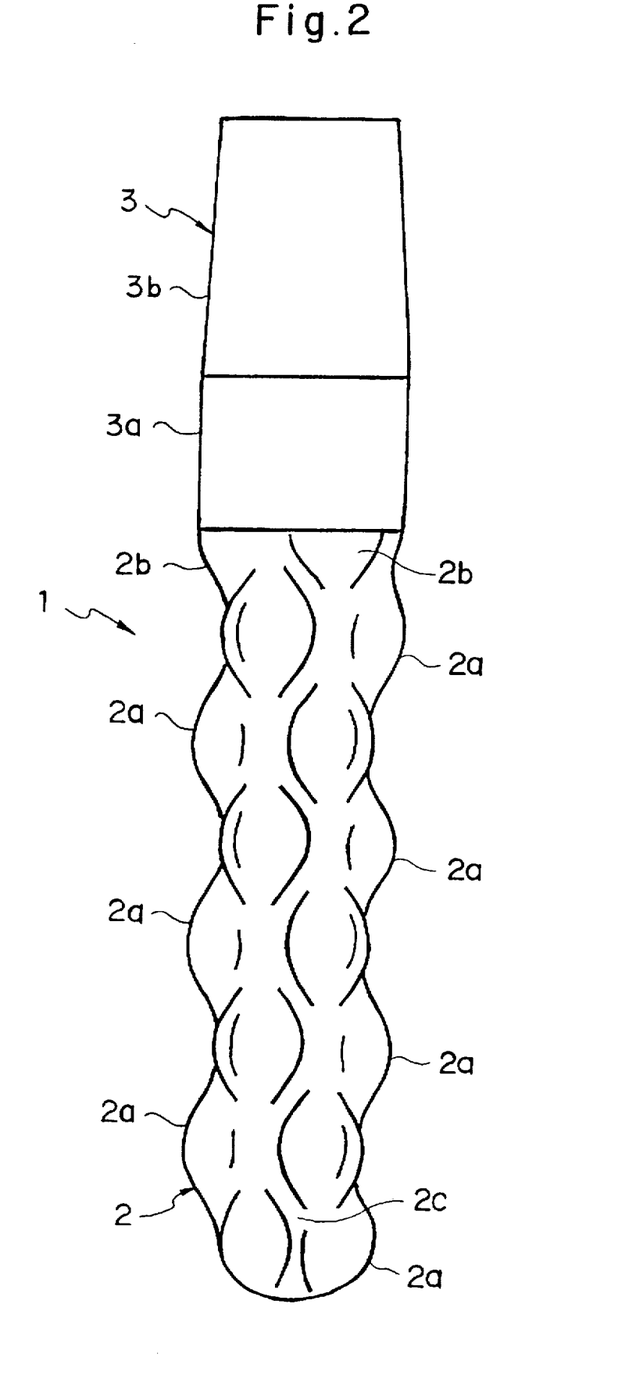
FIG. 2 is a side view of the artificial tooth root shown in FIG. 1.
Figure 3:
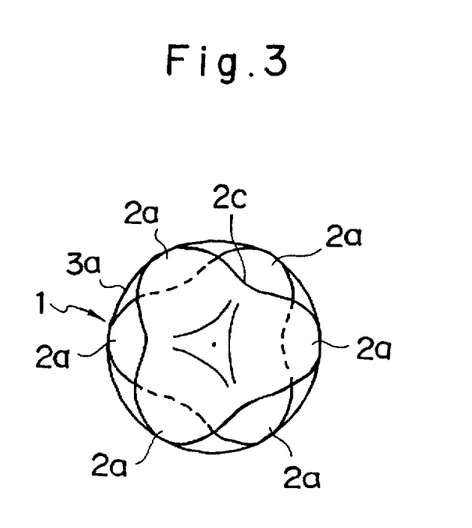
FIG. 3 is a bottom plan view of the artificial tooth root shown in FIG. 1.

In FIGS. 1 to 3 of the drawings, there is an illustrated artificial tooth root 1 according to a first embodiment of the invention, wherein convexities are formed. The artificial tooth root 1 comprises a root part 2 which is to be imbedded in a jaw bone, and a crown part 3 which is to be projected out of the jaw bone and on which is to be provided with a dental prosthesis. The crown part 3 comprising a cylindrical portion 3a and a truncated-conical portion 3b. The root part 2 is constituted by a base member 2c provided with three or four convexities 2a which are arranged with even intervals on each longitudinal axis apart from the central axis of the root part 2, and three convexities 2a which are arranged with even intervals on each circumference which is disposed along the direction of the axis.

The convexities 2a each of which is to be disposed on the other longitudinal axes which are placed at 60 degrees from said axis with the central axis of the cylindrical root part 2, are arranged with even intervals on the circumference located in the intermediate position between two neighboring convexities 2a arranged on the same axis. Hence, the convexities 2a on a circumference and the ones on the neighboring circumference are alternately arranged and are shifted through angle of 60 degrees with the central axis.

It is possible that the artificial tooth root 1 may be formed three or less incomplete convexities 2b with even intervals on circumferences in the end or in the end part on the side of the crown part 3, for the convenience of arrangement. Furthermore, smoothly curved surface throughout the root part 2 is formed by joining each convexity 2a and incomplete convexity 2b with the base member 2c of the root part 2 by smoothly curved surfaces.

In regard to the concrete size of the artificial tooth root 1, the outside maximum diameter of the root part is 4 mm, the convexity 2a has a spherical prominence of 0.7 mm in height, 1.5 mm in radius on the base member 2c which is made as a column with 2.6 mm diameter. Three convexities 2a are arranged with even intervals on a circumference of the base member 2c. The circumferences are arranged with 4 mm intervals along the central axis of the base member 2c. Three convexities 2a on a circumference and the ones on the neighboring circumference are alternately arranged and are shifted through angle of 60 degrees with the central axis of the base member 2c one another. The convexities 2a and the base member 2c being formed as mentioned above are joined by a smooth even surface which has uniform radius of curvature having substantially identical to that of the convexities 2a. Hence, a smooth and bumpy surface having substantially even radius of curvature can be obtained throughout the artificial tooth root 1.

The method of manufacturing the artificial tooth root 1 includes step of mixing powdery of titanium which is the material of the artificial tooth root 1 with a binder which is mainly composed of synthetic resin, and step of injection-molding the resultant mixture under a predetermined condition by the injection molding machine. This injection-molded article (which is called "green part" hereinafter) is worked by the dentist etc. so that it has such a size and a shape as fitted to each applied position (a diseased part) and the shape of which is furthermore adjusted in consideration of the particularity of each diseased part, and after this, the artificial tooth root 1 is completed by removing organic compounds from the green part and sintering it.

If the adjustment for the diseased part is not necessary, the artificial tooth root 1 may instantly be completed by removing the organic compounds and sintering the green part without the adjustment of the green part.

For the material of the artificial tooth root 1, titanium which is firm and high bio-compatible, is mainly used, and titanium oxide (TiO), aluminum oxide (AlO$_3$), hydroxy apatite or other materials having bio-compatibility are used as desired. The resin material which contains polypropylene, polyethylene and so on can mainly be used for the binder.

A split mold (is not shown in figure) for injection molding is used, and the number of segments is same as that of the convexities 2a and the incomplete convexities 2b formed on a circumference. The split mold for injection molding can be identically split by three planes passing through the central axis of the base member 2c, and the rows of peaks of the convexities 2a or the incomplete convexities 2b being located on the axes.

In the first embodiment having the above construction, the arrangement and the curvature of a plurality of convexities 2a, and the curvature of surface joining the boundaries between the convexities 2a and the base member 2c must properly be selected. Thus, even surface is formed on the root part 2, and surface throughout the root part 2 has substantially identical curvature. By removing the parts of very small curvature radius and harsh mannered parts, a load of the artificial tooth root 1 is uniformly and properly distributed and transmitted to the jaw bone. After implanting the artificial tooth root 1, such a tissue as a periodontal ligament effectively grows around the root part 2, and a connective tissue suitable for chewing can be obtained.

The plural smooth convexities 2a are formed on the imbedded part of the artificial tooth root 1 to be implanted on the diseased part. Hence, a load of the artificial tooth root 1 fixed to the jaw bone can effectively be distributed and a fine superficial bone can efficiently be grown along the surface around the imbedded part, and the artificial tooth root 1 can surely be held by growing a bone along the direction of longitudinal axis and around the circumference, distributing the load of the artificial tooth root 1 and transmitting to the jaw bone gives moderate stimulation to the circumferential bone and stimulate metabolism, and superficial bone around the imbedded part can be kept healthy.

As it is possible to form the smooth and bumpy surface with substantially identical curvature throughout the root part 2, so the artificial tooth root 1 can be facilitated to be formed without a undercut in case of injection molding and can easily be formed.

In order to obtain the artificial tooth root 1, a powder material and the binder are mixed and the green part of fixed shape is formed under a predetermined condition by injection into the split mold. After this, the split mold is disassembled and the green part is taken out. The green part which is adjusted so as to be suitable to each diseased part, is get rid of organic compounds in fireplace, is sintered, and the artificial tooth root 1 is produced as final products.

A second embodiment of the invention in which concavities are formed in place of the convexities of the first embodiment, is explained.

Figure 4:
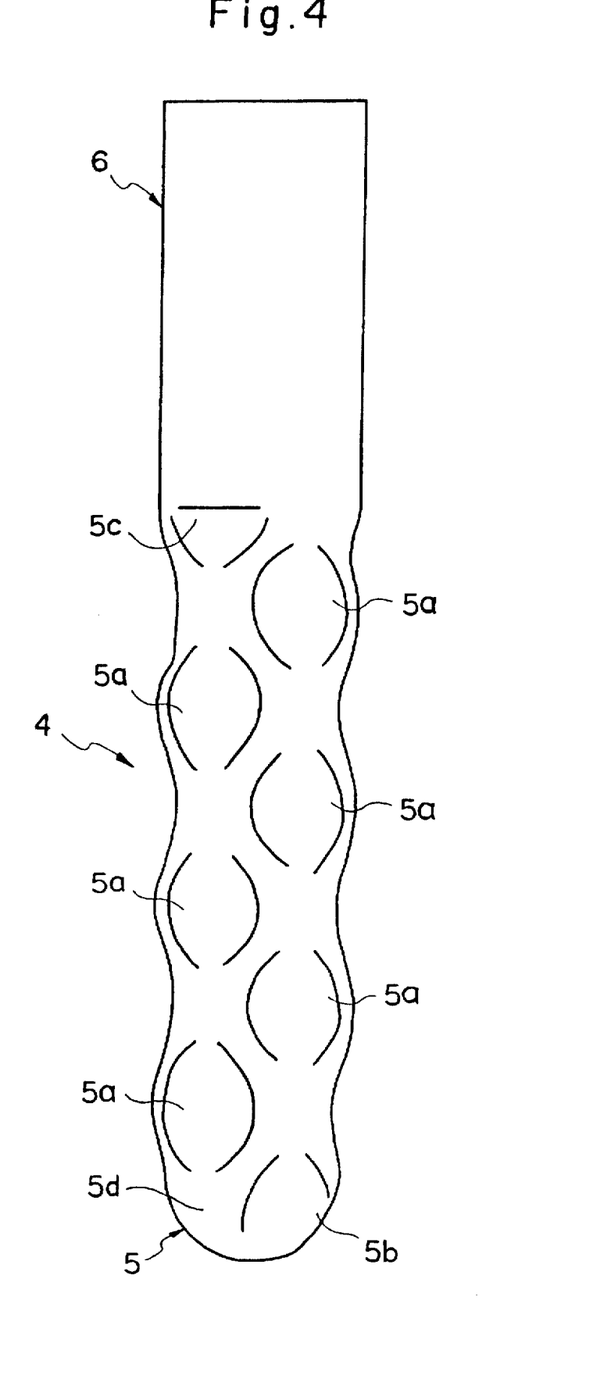
FIG. 4 is a side view of the artificial tooth root of tooth according to a second embodiment of the present invention.
Figure 5:
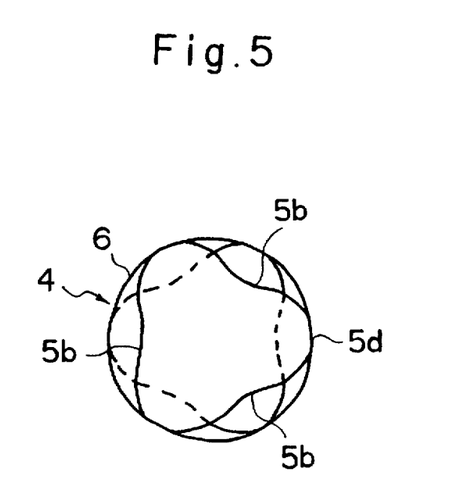
FIG. 5 is a bottom plan view of the artificial tooth root shown in FIG. 4.

FIGS. 4 to 5 show an artificial tooth root 4, on which concavities 5a are formed. Here, the artificial tooth root 4 comprises a root part 5 which is to be imbedded in a jaw bone, and a crown part 6 which is to be projected out of the jaw bone and on which is to be provided with a dental prosthesis. The crown part 6 is cylindrically formed.

The root part 5 is constituted by a base member 5d provided with three or four concavities 5a with even intervals on each longitudinal axis apart from the central axis of the root part 5 and three concavities 5a with even intervals on each circumference which is disposed along the direction of the axis.

The concavities 5a, each of which is to be disposed on the other axes which are placed at angle of 60 degrees from said axis with the central axis of the cylindrical root part 5, are arranged with even intervals on the circumference located in the intermediate position between two neighboring concavities 5a arranged on the same axis. Hence, the concavities 5a on a circumference and the ones on the neighboring circumference are alternately arranged and are shifted through angle of 60 degrees with the central axis.

It is possible that the artificial tooth root 4 may be formed three or less incomplete concavities 5b with even intervals on the circumference in the end or in the end part on the side of the crown part 6, for the convenience of arrangement. Furthermore, smooth curved surface throughout the root part 4 is formed by joining concavities 5a or incomplete convexities 5b with the base member 5c of the root part 5 by smoothly curved surface.

In regard to the concrete size of the artificial tooth root 4, the outside maximum diameter of the root part 5 is 4 mm, the concavity 5a has a spherical hollow of 0.7 mm in depth, 1.5 mm in radius on the base member 5d which is made as a column with 4 mm diameter. Three concavities 5a are arranged with even intervals on a circumference of the base member 5d. The circumferences are arranged with 4 mm intervals along the direction of axis. Three concavities 5a on a circumference and the ones on the neighboring circumference are alternately arranged and are shifted through angle of 60 degrees with the central axis of the cylindrical base member 5d one another. The boundaries between the concavities 5a or the incomplete concavities 5b, 5c and the base member 5d formed as mentioned above are joined by a smooth even surface which has uniform radius of curvature having substantially identical to that of the concavities. Hence, a smooth and bumpy surface having substantially even radius of curvature can be obtained throughout the artificial tooth root 4.

Besides, the manufacturing method of the second embodiment is same as that of the first embodiment except that the concavities are mounted in the mold in the place of the convexities. The effect of the second embodiment is same as that of the first embodiment except the difference of effect due to the difference between concavities and convexities.

Figure 6:
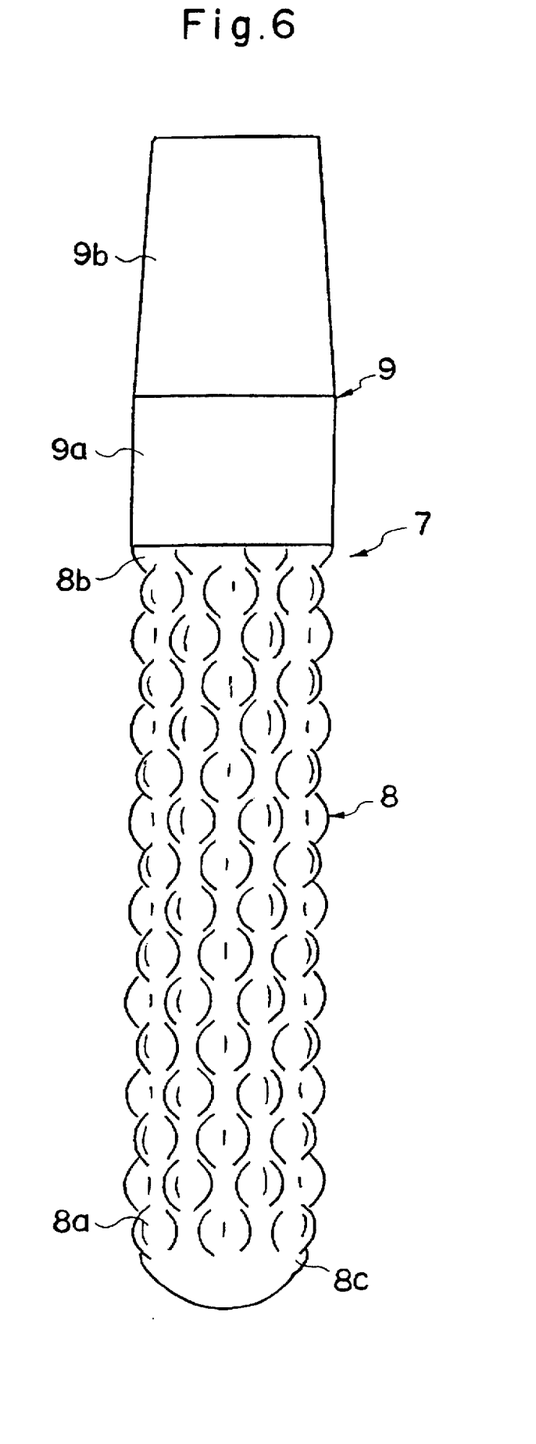
FIG. 6 is a side view of the artificial tooth root according to a third embodiment.
Figure 7:
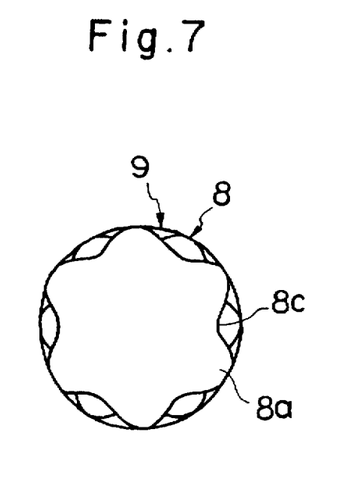
FIG. 7 is a bottom plan view of the artificial tooth root shown in FIG. 6.

A third embodiment of invention in which six convexities are formed on the same circumference in place of the first embodiment, is explained. FIGS. 6 to 7 show an artificial tooth root 7 which has six convexities 8a on a circumference of a root part 8. The artificial tooth root 7 comprises the root part 8 which is to be imbedded in a jaw bone and a crown part 9 which is to be projected out of the jaw bone and on which is to be provided with a dental prosthesis. The crown part 9 has a cylindrical part 9a and a truncated-conical part 9b.

The root part 8 is constituted by a base member 8c provided with eight convexities 8a with even intervals on each longitudinal axis apart from the central axis of the root part 8 and six convexities 8a with even intervals on each circumference which is disposed along the direction of the axis.

The convexities 8a, each of which is to be disposed on the other axes which are placed at angle of 30 degrees from said axis with the central axis of the cylindrical root part 8, are arranged with even intervals on the circumference located in the intermediate position between two neighboring convexities 8a arranged on the same axis. Hence, the convexities 8a on a circumference and the ones on the neighboring circumference are alternately arranged and are shifted through angle of 30 degrees with the central axis.

It is possible that the artificial tooth root 7 may be formed six or less incomplete convexities 8b with even intervals on the circumference in the end or in the end part on the side of the crown part 9, for the convenience of arrangement. Furthermore, smoothly curved surface is formed throughout the root part 8 by joining the boundaries between the convexity 8a or the incomplete convexity 8b and the base member 8c of the root part 8 by smoothly curved surface.

In regard to the concrete size of the artificial tooth root 7, the outside maximum diameter of the root part 8 is 4 mm, the convexity 8a has a spherical projection of 0.4 mm in height, 0.6 mm in radius on the base member 8c which is made as a column with 3.2 mm diameter. The convexities 8a are arranged with even intervals on the circumference of the base member 8c. The circumferences are arranged with 1.8 mm intervals along the central axis of the base member 8c. Six convexities on a circumference and the ones on the neighboring circumference are alternately arranged and are shifted through angle of 60 degrees with the central axis one another. The convexities 8a and the base member 8c being formed as mentioned above are joined by a smooth even surface which has uniform radius of curvature having substantially identical to that of the convexities 8a. Hence, a smooth and bumpy surface having substantially even radius of curvature can be obtained throughout the artificial tooth root 7.

Besides, the manufacturing method of the third embodiment is same as that of the first embodiment except that the form of a split mold is different and that a green part can sufficiently be removed by the split mold which can be split into three segments. This number of segments is different from six, which is the number of convexities 8a being disposed on a circumference with even interval. Furthermore, the effect of the manufacturing method of the third embodiment is same as that of the first embodiment except that the load of the artificial tooth root is finely and uniformly distributed and transmitted to the jaw bone by the reduction of size of the convexities 8a, and that the superficial bone can smoothly be grown.

The examples of the implant body with 4 mm diameter is shown above. However, an implant body with 5 mm diameter and 6 mm diameter and so on can be used, too. The smooth convexities or concavities with suitable size are formed in the surface of these implant body, and a load for the bone is effectively distributed and an undercut can be removed in case of injection molding. The above implant body is explained by such an example as the root part and the crown part is formed in a unitary body. However, the root part and the crown part is permitted to be made so as to be connected with separate bodies by screw and so on, or to be combined with them by gluing together. Also, the root part and the crown part can be formed so as to be free to be connected and separated.

Though it is explained that the number of convexities or concavities on a circumference is only three or six, in the above examples, the number is not limited to these cases. For example, the number of the convexity or concavity is permitted to be the case of four, five, seven, eight, or twelve etc. In these cases, for the same reason explained above, it is appropriate that a circumference on which convexities or concavities are arranged, is disposed in the intermediate position of each two neighboring convexities or concavities on the same axis apart from the central axis. The position of convexities or concavities on this circumference and that of the ones on the neighboring circumference along the direction of the axis are alternately arranged and are shifted through the angle which is a half of the interval between the neighboring convexities or concavities on a circumference. For the same reason explained in the case of three or six, in the case of eight, the artificial tooth root can be molded by a split mold which has four segments, and in the case of twelve, it can be molded by a split mold which has six segments, four segments, or three segments etc. without an undercut along the direction of split.

While the present invention has been illustrated and described with respect to some specific embodiment thereof, it is to be understood that the invention is by no means limited thereto but encompasses various changes and modifications which will become possible without departing from scope of the appended claims. Furthermore, the entire disclosure of Japanese Patent Application No. 8-132114 filed on May 27, 1996 including specification, claims, drawings and summary are incorporated herein by reference in entirety.

I claim:

1. An artificial tooth root comprising:

a substantially cylindrical root part to be imbedded in a jaw bone, and a substantially cylindrical crown part to be projected out of the jaw bone and to be provided with a dental prosthesis, wherein said root part is constituted by a base member provided with a multiplicity of convexities or concavities having substantially identical configuration and being disposed with even intervals on the same axis apart from the central axis of the root part and with even intervals on the same circumferences from a top to a bottom of the root part, the convexities or concavities on a circumference and the ones on the neighboring circumference are alternately arranged such that distances from the central axis to peaks of the convexities and bottoms of the concavities are substantially identical, and the boundaries between the convexities or concavities and the base member are formed by a smoothly curved surface.

2. The artificial tooth root according to claim 1, wherein the number of the convexities or concavities having substantially identical configuration, is a multiple of three.

3. The artificial tooth root according to claim 1, wherein said root part and said crown part are defined as a unitary body.

4. The artificial tooth root according to claim 1, wherein said root part and said crown part are defined as separate bodies and are free to be connected with each other and separated from each other.

5. The artificial tooth root according to claim 1, wherein said crown part has a cylindrical portion and a truncated-conical portion.

6. The artificial tooth root according to claim 1, wherein the number of the convexities or concavities to be disposed on the same circumference with even intervals is three, the convexities or concavities have a substantially identical configuration, the convexities or concavities to be disposed on the other axes to be placed at angle of 60 degrees from said axis with the central axis of cylindrical root part, are disposed on the circumference to be located in the intermediate position between two neighboring convexities or concavities on the same axis, and the convexities or concavities on a circumference and the ones on the neighboring circumferences are alternately arranged and are shifted through angle of 60 degrees with the central axis.

7. The artificial tooth root according to claim 1, wherein the number of the convexities or concavities which are disposed on the same circumference with even intervals is six, the convexities or concavities have a substantially identical configuration, the convexities or concavities to be disposed on the other axes to be placed at angle of 30 degrees from said axis with the central axis of cylindrical root part, are disposed on the circumference to be located in the intermediate position between two neighboring convexities or concavities on the same axis, and the convexities or concavities on a circumference and the ones on the neighboring circumferences are alternately arranged and are shifted through angle of 30 degrees with the central axis.

8. The artificial tooth root according to claim 1, wherein convexities or concavities and the base member are smoothly joined with uniform radius of curvature.

9. The artificial tooth root according to claim 1, wherein the root part is made of such farm and bio-compatible materials as aluminum, titanium oxide, or aluminum oxide.

10. An artificial tooth root comprising:

a substantially cylindrical root part to be imbedded in a jaw bone, the root part comprising:

a base member; and a plurality of convexities with substantially identical configurations evenly disposed along a central axis of the base member and each of the plurality of convexities is alternately arranged in relation to other convexities such that a distance from the central axis of the base member to each peak of the plurality of convexities is a constant value; and a substantially cylindrical crown part coupled to the root part and projecting out of the jaw bone and to be provided with a dental prosthesis.

11. The artificial tooth root of claim 10, wherein the number of convexities disposed on any circumference is three such that a central axis of each of the convexities disposed along a first circumference is disposed at an angle of 120 degrees from the central axis of other convexities located along the same circumference and each central axis of each of the convexities along the first circumference is disposed at and angle of 60 degrees from a central axis of adjacent convexities disposed on an adjacent circumference.

12. The artificial tooth root of claim 10, wherein the number of convexities disposed on any circumference is six such that a central axis of each of the convexities disposed along a first circumference is disposed at an angle of 60 degrees from the central axis of adjacent convexities located along the same circumference and each central axis of each of the convexities along the first circumference is disposed at and angle of 30 degrees from a central axis of adjacent convexities disposed on an adjacent circumference.

* * * * *